United States Patent [19]

Parmigiani

[11] Patent Number: 5,607,398
[45] Date of Patent: Mar. 4, 1997

[54] HOLDING DEVICE FOR A NEEDLE PENETRATABLE INTO THE BODY

[75] Inventor: Corrado S. Parmigiani, Correggio, Italy

[73] Assignee: C.G.M. S.p.A., Via Modena, Italy

[21] Appl. No.: 467,806

[22] Filed: Jun. 6, 1995

[51] Int. Cl.⁶ ................................. A61M 25/06
[52] U.S. Cl. ......................... 604/177; 604/174
[58] Field of Search .................... 604/174, 175, 604/177, 264, 280; 128/DIG. 26

[56] References Cited

U.S. PATENT DOCUMENTS

| | | | |
|---|---|---|---|
| 4,161,177 | 7/1979 | Fuchs | 604/177 |
| 4,389,210 | 6/1983 | Genese | 604/177 |
| 4,392,856 | 7/1983 | Lichtenstein | 604/177 |
| 4,435,175 | 3/1984 | Friden | 604/177 |
| 4,863,432 | 9/1989 | Kvalo | 604/177 |
| 4,888,001 | 12/1989 | Schoenberg . | |
| 5,147,319 | 9/1992 | Ishikawa et al. | 604/174 |
| 5,149,328 | 9/1992 | Zaha | 604/174 X |
| 5,163,913 | 11/1992 | Rantanen-Lee et al. | 604/177 |
| 5,382,240 | 1/1995 | Lam | 604/177 |

FOREIGN PATENT DOCUMENTS

| | | | |
|---|---|---|---|
| 337606 | 10/1989 | European Pat. Off. | 604/174 |
| 0353916 | 7/1990 | European Pat. Off. . | |
| 2011885 | 7/1992 | European Pat. Off. | 604/177 |
| 0589506 | 3/1994 | European Pat. Off. . | |
| 92A000075 | 7/1995 | Italy . | |

*Primary Examiner*—Sam Rimell

[57] ABSTRACT

A front element not constrained to the front portion of the needle is provided, foldable on itself about a first folding axis parallel to the front portion. The rear portion of the needle is constrained to the front element such that the needle can rotate with respect to the front element about a second folding axis perpendicular to the needle. The device can assume a first operating configuration in which the element is folded on itself by rotation about the first axis, with the front portion of the needle enclosed between the two fins of the element, these facing each other and being close together. The device includes an elastically soft layer applied to the inner surface of the front element in correspondence at least with the final portion of the needle. When the front element is folded on itself into the first configuration this layer presses against the final portion of the needle to close its mouth opening.

15 Claims, 3 Drawing Sheets

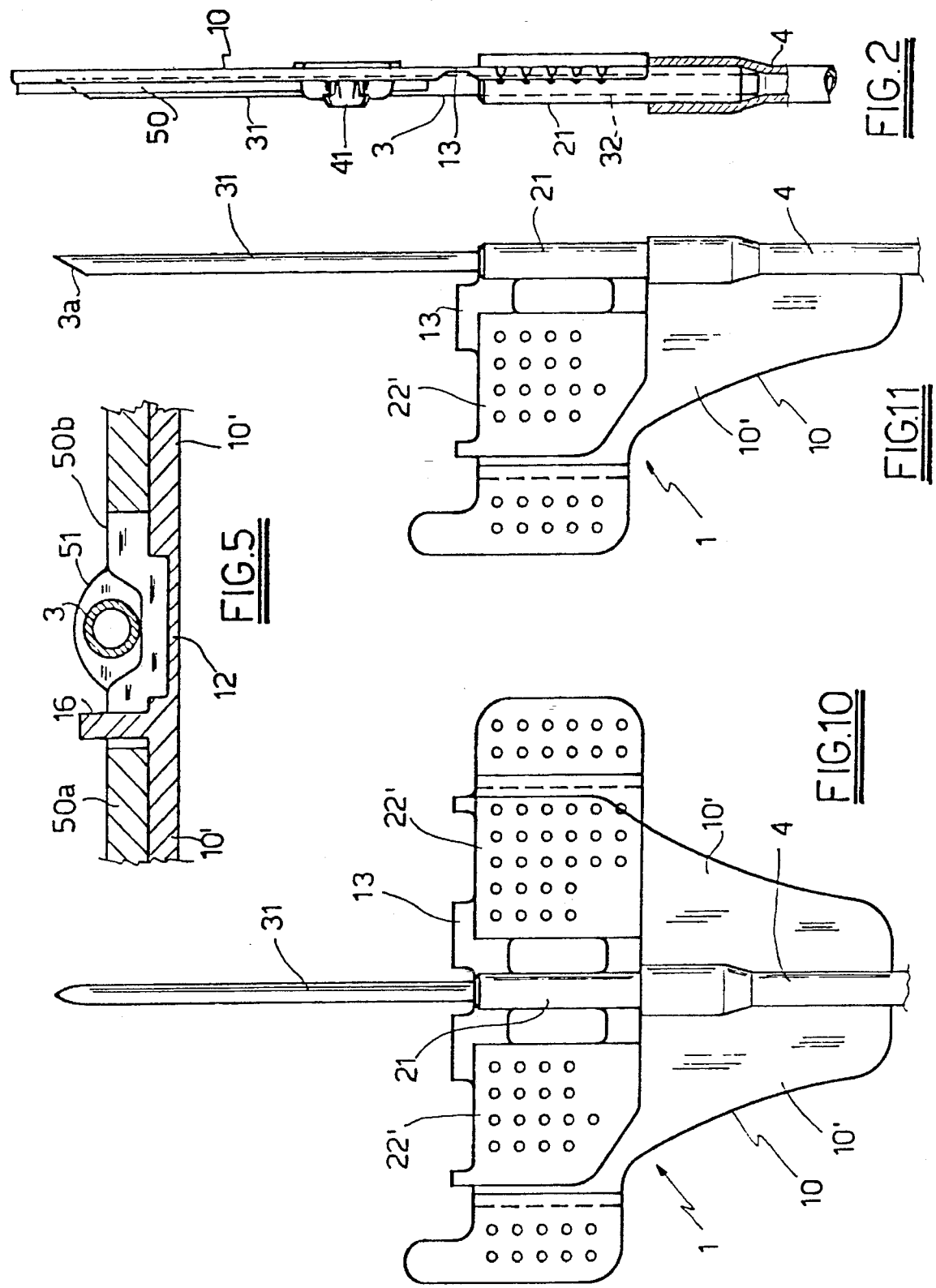

1

HOLDING DEVICE FOR A NEEDLE PENETRATABLE INTO THE BODY

BACKGROUND OF THE INVENTION

1. Field of the Invention

This invention relates to a needle holding device for needles which penetrate into the body and are connected to a thin flexible tube, in particular for needles for infusion, sampling and similar uses.

2. Description of the Background Art

In patent application Ser. No. RE 92A000075 in the name of the present applicant, a needle holding device is illustrated which effectively solves the problem of protection against pricking by the needle when this has been inserted into and then withdrawn from the patient's body.

The device illustrated in the aforementioned patent application comprises a front element, in particular in the form of a small thin elastic plate, which is positioned adjacent to the front portion of the needle and is foldable on itself about a first folding axis parallel to the front portion of the needle. The front portion of the needle is not constrained to this front element; instead, to this there is constrained the rear portion of the needle by suitable means enabling the needle to be rotated with respect to the front element about a second folding axis substantially perpendicular to the first axis.

This device can assume a first operating configuration in which the front element is folded on itself, by rotation about the first axis, with the front portion of the needle enclosed between the two mutually facing fins of the front element, and the needle point not projecting from the element.

The device can also assume a second operating configuration, by rotating the front element with respect to the needle about the second axis, in which the front portion of the needle projects freely from the front element.

Means are also provided for constraining the two mutually facing fins of the front element together, with the facility for their separation, when this is positioned in the first operating configuration.

When in use, the device is folded into the second operating configuration so that the front portion of the needle is free. After the needle has been extracted from the patient the device is put into the first operating configuration to enclose the needle point and protect persons from the risk of pricking.

SUMMARY OF THE INVENTION

The present invention proposes to improve the above needle holding device such as to increase protection against other dangers. In this respect, in many applications the patient's blood enters the needle and possibly also the tube connected to it, such as when taking blood samples, or in certain cases of infusion, or other such cases.

In all these cases, when the needle has been extracted from the patient there is a risk that blood droplets originating from the needle can make contact with persons in the vicinity, with consequent danger to their health especially if infection is involved.

The object of the present invention is therefore to improve the needle holding device of the aforesaid type so that it also offers protection against the above danger represented by blood present in the needle.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention is described in detail hereinafter with reference to the accompanying figures, which illustrate a preferred embodiment thereof, and wherein:

FIG. 2 is a side view of FIG. 1.

FIG. 5 is a section on the plane V—V of FIG. 1.

FIG. 10 is a plan view as in FIG. 1, showing the device in the second operating configuration.

FIG. 11 is a side view of the device in a more folded state than FIG. 10.

DETAILED DESCRIPTION OF THE PREFERRED EMBODIMENTS

Figures 1, 3, 4:
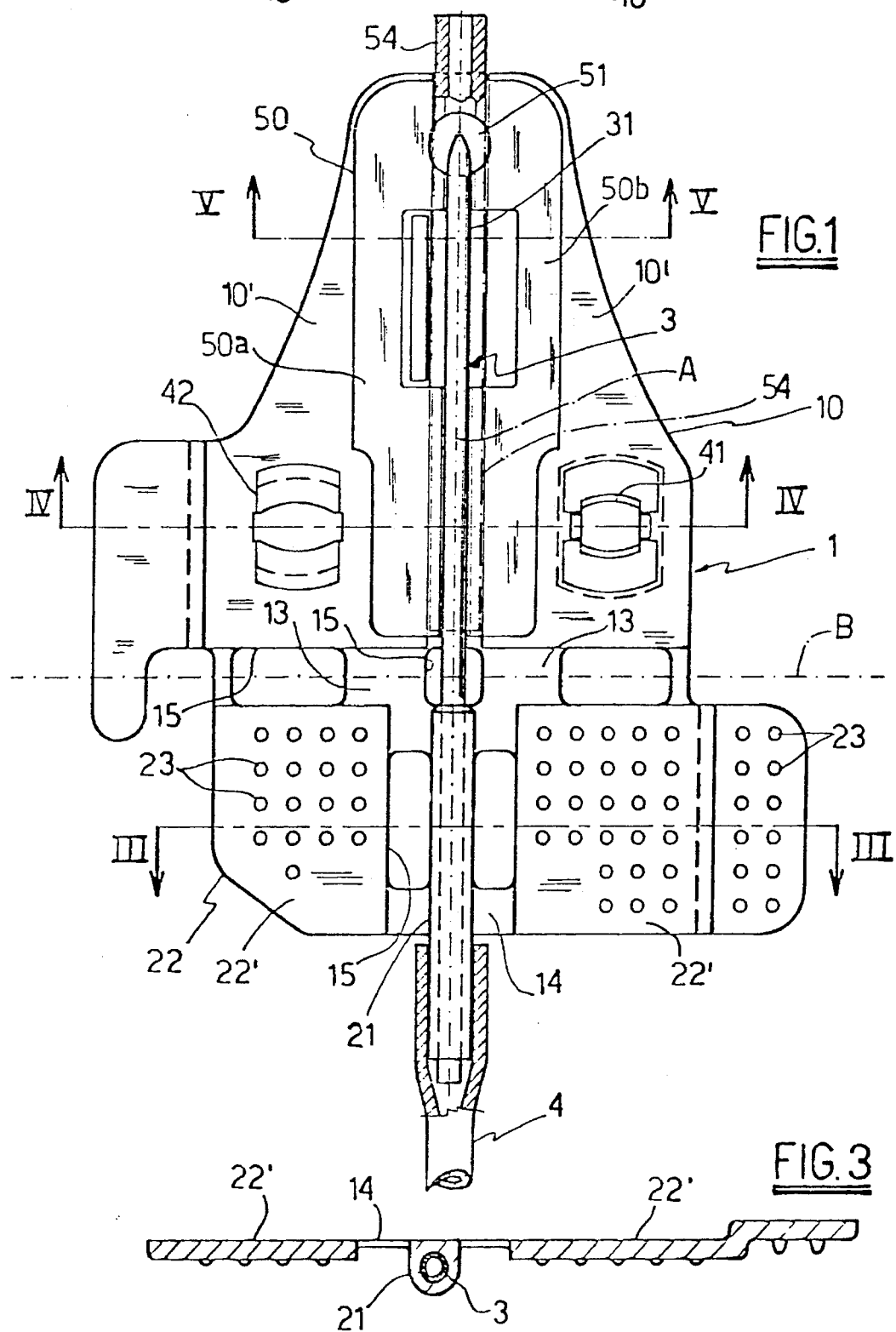
FIG. 1 is an enlarged plan view of the device in its open configuration.
FIG. 3 is a section on the plane III—III of FIG. 1.
FIG. 4 is a section on the plane IV—IV of FIG. 1.

In the figures, the needle holding device of the invention is indicated overall by 1, while 3 indicates the needle for penetration into the body and comprises a front portion 31 provided with a point (at which the exit mouth 3a of the needle internal channel is located) and a rear portion 32 which is connected to a rear tube 4 for connection to the needle 3.

The device 1 comprises a front element 10 positioned adjacent to the front portion 31 of the needle but not constrained thereto; the element 10 can be folded on .itself substantially about a first folding axis A parallel and adjacent to the portion 31. Means (described in detail hereinafter) are also provided for constraining the rear portion 32 to the front element 10 so that the needle 3 can rotate with respect to the element 10 substantially about a second axis B substantially perpendicular to the needle 3.

The term "folding axis" means either a true axis of rotation about which two rigid bodies rotate (in the case of two rigid bodies articulatedly connected together) or a more or less wide folding region extending axially along said axis, along which a body deforms by flexure (in the case of a single flexible body). The device 1 can assume a first operating configuration (FIGS. 6, 7, 8, 9) in which the element 10 is folded on itself by being folded about the first axis A, the front portion 31 being enclosed between the two lateral fins 10' of the element 10 (the two portions of the element 10 separated by the first axis A), which face each other in mutual contact; the form and dimensions of the element 10 with reference to the needle 3 are such that when in this configuration, the point of the needle 3 does not project beyond the element 10.

The device 1 can also assume a second operating configuration (FIG. 10) achieved by folding the element 10 relative to the needle 3 about the second axis B, in which the front portion 31 projects freely from the element 10. When in this second configuration the element 10 can be further folded on itself about the first axis A (FIG. 11) so as to be able to be comfortably gripped between two fingers for its insertion into the patient's body; alternatively it can be left open (FIGS. 7 and 13), to be rested on the surface of the body and fixed thereto by adhesive tape.

Preferably the element 10 is in the form of a thin plate sufficiently rigid to the extent that in normal use it cannot undergo deformation such as to enable the point of the needle 3 to project beyond the element 10 when in its first configuration. In practice this can be achieved by constructing the element 10 or indeed the entire device 1 of synthetic resin by a moulding process.

The rotation about the first axis A can be achieved by providing a suitable folding region 12 coaxial to the axis A, in which the thickness of the element 10 is reduced, the material with which the element 10 is formed being sufficiently flexible to allow bending along this line.

In the illustrated embodiment, the constraining means includes a bush 21 which surrounds, and is rigidly joined to, the rear portion 32 of the needle 3, and a rear element 22 in the form of a thin plate which is joined to the bush 21 in a manner substantially coplanar therewith and is joined to the front element 10 in a manner substantially coplanar therewith by thin flexible portions 13. The rear element 22 is foldable on itself about an axis substantially coinciding with the first axis A; for this purpose it comprises a folding region 14 in the connection region between the element 22 and the bush 21. The flexible portions 13 enable the rear element 22, and hence the needle 3, to rotate relative to the front element 10 about the second axis B.

The rear element 22 is divided into two lateral fins 22' by the folding region 14.

When the device 1 is folded into its second configuration, the front element 10 faces and is in contact with the rear element 22, whereas the front portion 31 of the needle 3 projects completely beyond the device 1 and can hence be inserted into the patient's body; the two elements 10 and 22 can be further folded together, by rotation about the axis A along the respective folding regions 12 and 14 which in this case are mutually superposed (FIG. 11).

The folding regions 12 and 14 are defined by regions of smaller thickness than the surrounding regions and located along a narrow central longitudinal portion parallel to the axis A and to which the bush 21 is joined to form a single piece therewith in the case of the element 22, whereas it faces the front portion 31 in the case of the element 10.

Means are provided for disengagably constraining to each other the two mutually facing fins 10' of the front element 10 when in the first operating configuration.

Figure 9:
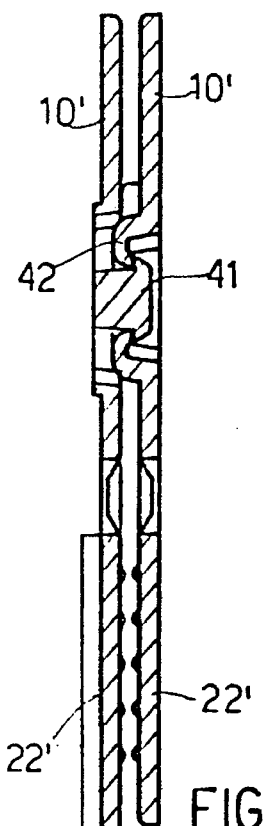
FIG. 9 is a section on the plane IX—IX of FIG. 6.
Figure 6:
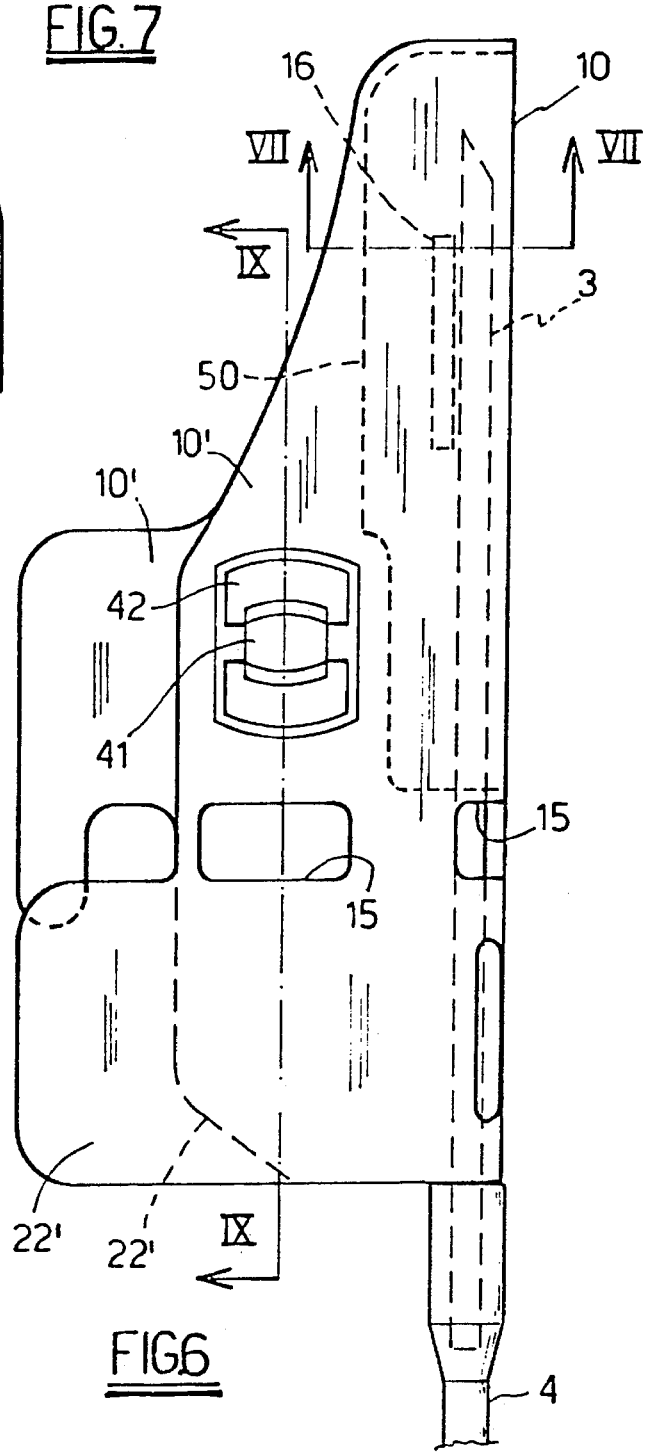
FIG. 6 is a side view of the device in its first operating configuration.

In the illustrated embodiment, said means comprise a male element 41 positioned on one of the two fins 10' and projecting outwards from the inner surface of the element 10 (i.e. that surface which is internal when the element 10 is folded into the first operating configuration), for engagement with a corresponding female element 42 located on the other fin 10' in a position symmetrical with the element 41 about the axis A. The two elements 41 and 42 snap-fit together (in the manner of a press-stud) by slight forcing, so as to securely maintain the two fins 10' mutually constrained one against the other (FIG. 9). The elements 41 and 42 also serve to constrain the two fins 10' together when the device is folded into the second operating configuration shown in FIG. 11.

To use the needle, the element 10 is folded about the axis B to bring it into the second operating configuration and allow the front portion 31 to project freely.

After further folding the elements 10 and 22 about the axis A (FIGS. 8 and 9), the device 1 can be comfortably gripped by two fingers to introduce the needle into the body. After this, the elements 10 and 22 can be opened mutually coplanar, to be rested on the surface of the body and be fixed thereto. Finally, when the needle 3 has been extracted from the patient's body, the element 10 can be returned to the first configuration to enclose the needle point, after which the device 1 can be disposed of in the refuse, with the relative needle protected.

All the described operations can be comfortably and easily effected without the operator's fingers touching the needle, in particular its point, and hence with no danger of pricking. In addition, when the needle 3 has been thrown into the refuse, it is protected by the device 1 and can be disposed of without danger of pricking other persons.

The entire device 1 can be advantageously constructed in one piece from synthetic resin by a moulding process.

On the rear element 22 there are provided numerous small projections 23 to make the surface of the element 22 rougher and allow more secure grippage by the fingers.

In the folding regions 13 and 14 there are provided apertures 15 to make these regions more easily flexible.

According to the present invention, on the inner surface of the front element 10 there is applied an elastically soft layer 50 in correspondence at least with the final portion of the needle. When the front element 10 is folded on itself about the axis A, the layer 50 deforms against the needle, to press against its final portion and close the exit mouth 3a.

Specifically, in the illustrated embodiment, the layer 50 comprises two portions 50a and 50b positioned on one and the other side of the folding axis A, they being arranged to press one against the other with the final portion of the needle 3 interposed, when the element 10 is in the first operating configuration.

Preferably, the layer 50 is also provided on the folding region 12. Advantageously, at the point of the needle 3, in correspondence with the needle mouth 3a, the layer 50 comprises an outwardly projecting greater-thickness portion 51 against which the needle mouth 3a presses when the device is in the first configuration (FIG. 8).

Joined to the inner surface of the front element 10 (in particular in one piece with it) there can also be provided a projection 16 which projects outwards from this surface and extends parallel and close to the front portion 31 of the needle.

Figure 7:
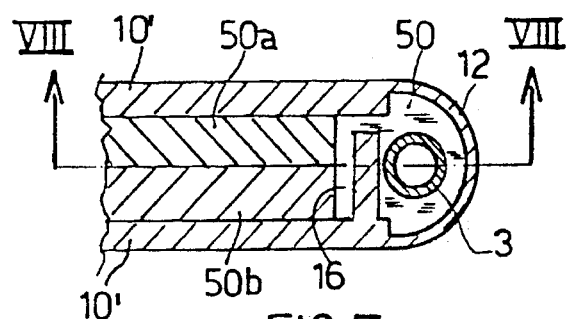
FIG. 7 is a section on the plane VII—VII of FIG. 6.
Figure 8:
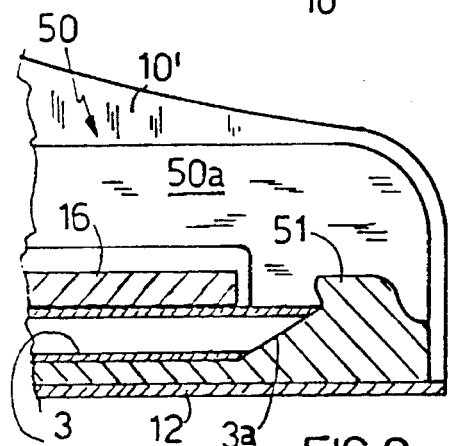
FIG. 8 is a section on the plane VIII—VIII of FIG. 7.

When the front element 10 is folded into the first configuration, the projection 16 abuts against the front portion 31 to maintain it pressed against that part of the layer 50 provided in the folding region 12 and in particular to keep the mouth 3a pressed against the projecting portion 51 (FIGS. 7, 8). In this manner, the projection 16 prevents the front portion 31 from separating from the folding region 12. The layer 50 can be lacking in the region comprising the projection 16, to allow correct positioning of the projection 16.

Advantageously, the layer 50 can involve not only the point of the needle 3 but virtually its entire front portion 31.

The layer 50 can be formed of expanded synthetic resin, preferably of closed-cell type, to create an impermeable protection about the needle.

Alternatively the layer 50 can be formed of relatively very yieldable elastomer.

In use, after the needle 3 has been extracted from the patient's body, the element 10 is folded into the first operating configuration as heretofore described.

In this configuration, the layer 50 surrounds the front portion 31 of the needle and in particular its final mouth (FIGS. 7, 8). Consequently any blood present in the needle or tube 4 cannot escape from the needle and hence is unable to come into contact with persons in the vicinity. In the same manner, any blood present on the outer surface of the needle 3 is enclosed by the layer 50 and is hence unable to come into contact with persons.

All risk of infection or the like is hence eliminated.

Before the needle is used in a patient's body, a thin tubular element 54 (shown only in FIG. 1) can be associated with the needle such as to surround its front portion 31. The tubular element 54 has its front portion slightly emerging from the soft element 50 and also from the front element 10.

The purpose of the element 54 is to prevent small particles of the soft layer 50 penetrating into the final mouth of the needle 3, to then be introduced into the patient's body, and to ensure that the final mouth of the needle 3 does not become closed by the layer 50 and prevent pressurized sterilizing gas entering the needle, as required during sterilization. The element 54 is removed to allow the needle to be inserted into the patient's body, and is then disposed of.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A holding device for a needle, said needle including a front portion and a rear portion, said front portion having a tip with an opening therein, said holding device comprising:

a front element positioned adjacent to the front portion of the needle, said front element including a pair of fins and being foldable on itself about a first folding axis substantially parallel to the front portion of the needle;

means for attaching the rear portion of the needle to the front element so that the needle can rotate with respect to the front element about a second folding axis substantially perpendicular to the needle, the device being able to assume a first configuration in which the front element is folded on itself by rotation about said first folding axis, with the front portion of the needle enclosed between the pair of fins of the front element, the tip of the needle not projecting from the front element; and an elastic layer located on an inner surface of the front element adjacent to the front portion of the needle, said elastic layer being arranged, when the front element is folded on itself into the first configuration, to press against the front portion of the needle to thereby surround the front portion of the needle and close the opening in the tip of the needle.

2. The device as claimed in claim 1, wherein said elastic layer includes first and second portions arranged on opposed sides of the first folding axis for being pressed against one another when in said first configuration.

3. The device as claimed in claim 1, wherein said elastic layer substantially encloses the front portion of the needle when the front element is in said first configuration.

4. The device as claimed in claim 1 further comprising a thin tubular element surrounding the tip of the needle and, when the front element is in said first configuration, enclosed by the front element and by said elastic layer, with its front end emerging from said soft layer.

5. The device as claimed in claim 1, wherein said elastic layer is made of expanded synthetic resin.

6. The device as claimed in claim 5, wherein said expanded synthetic resin is a closed cell resin.

7. The device as claimed in claim 1, wherein the elastic layer comprises an outwardly projecting greater-thickness portion against which the opening in the tip of the needle presses when the front element is in the first configuration.

8. The device as claimed in claim 1, further comprising a projection attached to the inner surface of the front element and projecting outwardly from said inner surface to extend parallel and close to the front portion of the needle in order to press said front portion against part of the elastic layer positioned along the first folding axis.

9. The device as claimed in claim 1, further comprising means for selectively constraining the fins together when the front element is in the first configuration.

10. The device as claimed in claim 1, wherein said elastic layer includes first and second portions arranged on opposed sides of the first folding axis for being pressed against one another when in said first configuration, and wherein said elastic layer substantially encloses the front portion of the needle when the front element is in said first configuration.

11. The device as claimed in claim 10, further comprising means for selectively constraining the fins together when the front element is in the first configuration.

12. The device as claimed in claim 11, further comprising a projection attached to the inner surface of the front element and projecting outwardly from said inner surface to extend parallel and close to the front portion of the needle in order to press said front portion against part of the elastic layer positioned along the first folding axis.

13. The device as claimed in claim 12, wherein the elastic layer comprises an outwardly projecting greater-thickness portion against which the opening in the tip of the needle presses when the front element is in the first configuration.

14. The device as claimed in claim 13, wherein said elastic layer is made of expanded synthetic resin.

15. The device as claimed in claim 14, wherein said expanded synthetic resin is a closed cell resin.

* * * * *